United States Patent [19]
Adamec

[11] Patent Number: 5,948,010
[45] Date of Patent: Sep. 7, 1999

[54] THERAPEUTIC HEAT APPLICATION DEVICE

[76] Inventor: Norine A. Adamec, 235 S. Westcott Rd., Schenectady, N.Y. 12306

[21] Appl. No.: 09/130,441

[22] Filed: Aug. 6, 1998

[51] Int. Cl.$^6$ ...................................................... A61F 7/00
[52] U.S. Cl. ............................. 607/96; 607/108; 607/112
[58] Field of Search ............................. 607/96, 108, 109, 607/110, 111, 112; 383/901; 206/438; 165/46

[56] References Cited

U.S. PATENT DOCUMENTS

| | | | |
|---|---|---|---|
| 2,497,443 | 2/1950 | Eatman | 607/108 |
| 5,603,727 | 2/1997 | Clark et al. | 607/108 |

*Primary Examiner*—Linda C. M. Dvorak
*Assistant Examiner*—Rosiland Kearney

[57] ABSTRACT

A new therapeutic heat application device for applying heat to various areas of a person's body. The inventive device includes a pad portion having a wide central portion and a pair of opposed tapered side portions. The pad portion has a shape resembling a pair of lips. The wide central portion is divided into a plurality of narrow sections by vertically extending seams. Each of the tapered side portions is divided into two sections by a horizontally extending seam. The sections of the wide central portion and the tapered side portions are filled with cracked corn. A pair of straps extend outwardly from the tapered side portions of the pad portion. Each of the straps have hook and loop fasteners disposed thereon for engaging each other when the straps wrap the pad portion around a body of a wearer.

4 Claims, 2 Drawing Sheets

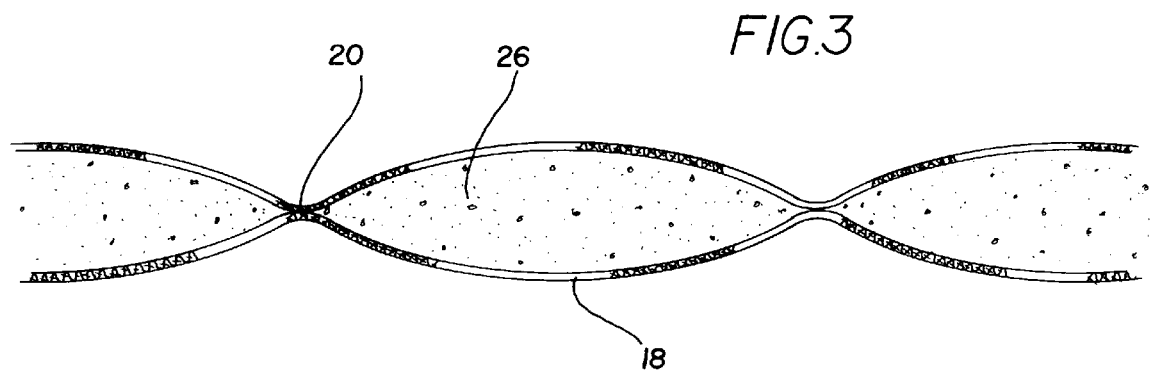
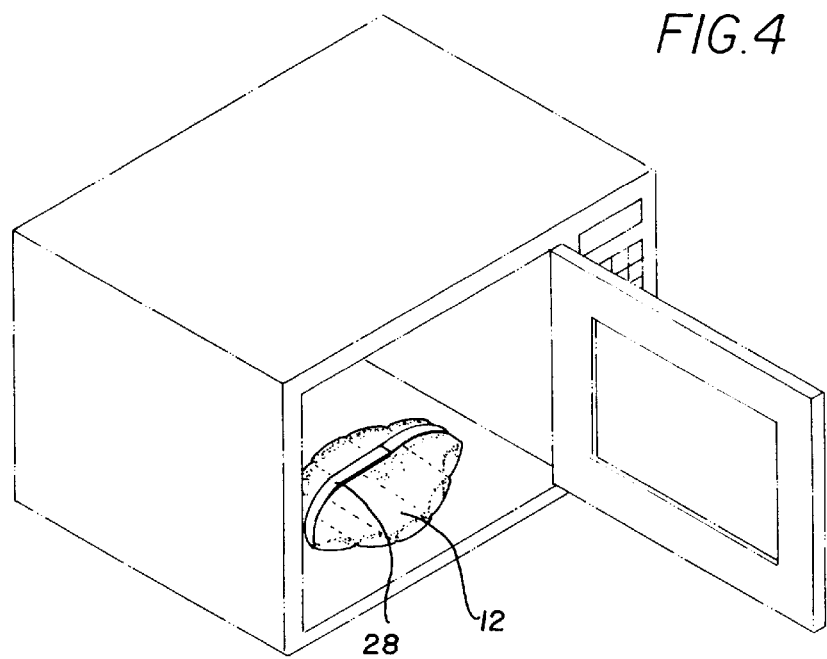

THERAPEUTIC HEAT APPLICATION DEVICE

BACKGROUND OF THE INVENTION

1. Field of the Invention

The present invention relates to heating pads and more particularly pertains to a new therapeutic heat application device for applying heat to various areas of a person's body.

2. Description of the Prior Art

The use of heating pads is known in the prior art. More specifically, heating pads heretofore devised and utilized are known to consist basically of familiar, expected and obvious structural configurations, notwithstanding the myriad of designs encompassed by the crowded prior art which have been developed for the fulfillment of countless objectives and requirements.

Known prior art heating pads include U.S. Pat. No. 5,179,944 to McSymytz; U.S. Pat. No. 5,300,105 to Owens; U.S. Pat. No. Des. 353,205 to Canavan; U.S. Pat. No. 2,590,212 to Samuels; U.S. Pat. No. 3,407,818 to Costanzo; Patent No. WO 92/19201 to Peters; and Patent No. EP 0 435 463 Al to McKenzie et al.

While these devices fulfill their respective, particular objectives and requirements, the aforementioned patents do not disclose a new therapeutic heat application device. The inventive device includes a pad portion having a wide central portion and a pair of opposed tapered side portions. The pad portion has a shape resembling a pair of lips. The wide central portion is divided into a plurality of narrow sections by vertically extending seams. Each of the tapered side portions is divided into two sections by a horizontally extending seam. The sections of the wide central portion and the tapered side portions are filled with cracked corn. A pair of straps extend outwardly from the tapered side portions of the pad portion. Each of the straps have hook and loop fasteners disposed thereon for engaging each other when the straps wrap the pad portion around a body of a wearer.

In these respects, the therapeutic heat application device according to the present invention substantially departs from the conventional concepts and designs of the prior art, and in so doing provides an apparatus primarily developed for the purpose of applying heat to various areas of a person's body.

SUMMARY OF THE INVENTION

In view of the foregoing disadvantages inherent in the known types of heating pads now present in the prior art, the present invention provides a new therapeutic heat application device construction wherein the same can be utilized for applying heat to various areas of a person's body.

The general purpose of the present invention, which will be described subsequently in greater detail, is to provide a new therapeutic heat application device apparatus and method which has many of the advantages of the heating pads mentioned heretofore and many novel features that result in a new therapeutic heat application device which is not anticipated, rendered obvious, suggested, or even implied by any of the prior art heating pads, either alone or in any combination thereof.

To attain this, the present invention generally comprises a pad portion having a wide central portion and a pair of opposed tapered side portions. The pad portion has a shape resembling a pair of lips. The wide central portion is divided into a plurality of narrow sections by vertically extending seams. Each of the tapered side portions is divided into two sections by a horizontally extending seam. The sections of the wide central portion and the tapered side portions are filled with cracked corn. A pair of straps extend outwardly from the tapered side portions of the pad portion. Each of the straps have hook and loop fasteners disposed thereon for engaging each other when the straps wrap the pad portion around a body of a wearer.

There has thus been outlined, rather broadly, the more important features of the invention in order that the detailed description thereof that follows may be better understood, and in order that the present contribution to the art may be better appreciated. There are additional features of the invention that will be described hereinafter and which will form the subject matter of the claims appended hereto.

In this respect, before explaining at least one embodiment of the invention in detail, it is to be understood that the invention is not limited in its application to the details of construction and to the arrangements of the components set forth in the following description or illustrated in the drawings. The invention is capable of other embodiments and of being practiced and carried out in various ways. Also, it is to be understood that the phraseology and terminology employed herein are for the purpose of description and should not be regarded as limiting.

As such, those skilled in the art will appreciate that the conception, upon which this disclosure is based, may readily be utilized as a basis for the designing of other structures, methods and systems for carrying out the several purposes of the present invention. It is important, therefore, that the claims be regarded as including such equivalent constructions insofar as they do not depart from the spirit and scope of the present invention.

Further, the purpose of the foregoing abstract is to enable the U.S. Patent and Trademark Office and the public generally, and especially the scientists, engineers and practitioners in the art who are not familiar with patent or legal terms or phraseology, to determine quickly from a cursory inspection the nature and essence of the technical disclosure of the application. The abstract is neither intended to define the invention of the application, which is measured by the claims, nor is it intended to be limiting as to the scope of the invention in any way.

It is therefore an object of the present invention to provide a new therapeutic heat application device apparatus and method which has many of the advantages of the heating pads mentioned heretofore and many novel features that result in a new therapeutic heat application device which is not anticipated, rendered obvious, suggested, or even implied by any of the prior art heating pads, either alone or in any combination thereof.

It is another object of the present invention to provide a new therapeutic heat application device which may be easily and efficiently manufactured and marketed.

It is a further object of the present invention to provide a new therapeutic heat application device which is of a durable and reliable construction.

An even further object of the present invention is to provide a new therapeutic heat application device which is susceptible of a low cost of manufacture with regard to both materials and labor, and which accordingly is then susceptible of low prices of sale to the consuming public, thereby making such therapeutic heat application device economically available to the buying public.

Still yet another object of the present invention is to provide a new therapeutic heat application device which provides in the apparatuses and methods of the prior art some of the advantages thereof, while simultaneously overcoming some of the disadvantages normally associated therewith.

Still another object of the present invention is to provide a new therapeutic heat application device for applying heat to various areas of a person's body.

Yet another object of the present invention is to provide a new therapeutic heat application device which includes a pad portion having a wide central portion and a pair of opposed tapered side portions. The pad portion has a shape resembling a pair of lips. The wide central portion is divided into a plurality of narrow sections by vertically extending seams. Each of the tapered side portions is divided into two sections by a horizontally extending seam. The sections of the wide central portion and the tapered side portions are filled with cracked corn. A pair of straps extend outwardly from the tapered side portions of the pad portion. Each of the straps have hook and loop fasteners disposed thereon for engaging each other when the straps wrap the pad portion around a body of a wearer.

These together with other objects of the invention, along with the various features of novelty which characterize the invention, are pointed out with particularity in the claims annexed to and forming a part of this disclosure. For a better understanding of the invention, its operating advantages and the specific objects attained by its uses, reference should be made to the accompanying drawings and descriptive matter in which there are illustrated preferred embodiments of the invention.

BRIEF DESCRIPTION OF THE DRAWINGS

The invention will be better understood and objects other than those set forth above will become apparent when consideration is given to the following detailed description thereof. Such description makes reference to the annexed drawings wherein:

FIG. 3 is a cross-sectional view of the present invention as taken along line 3—3 of FIG. 2.

FIG. 4 is a perspective view of the present invention illustrated being heated in a microwave oven.

DESCRIPTION OF THE PREFERRED EMBODIMENT

Figure 1:
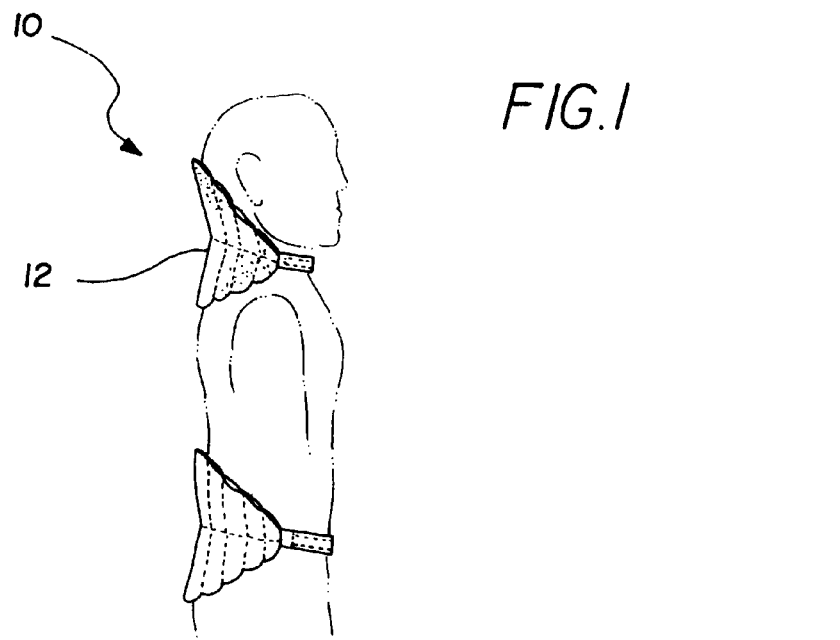
FIG. 1 is a side view of a new therapeutic heat application device according to the present invention illustrated in use.
Figure 2:
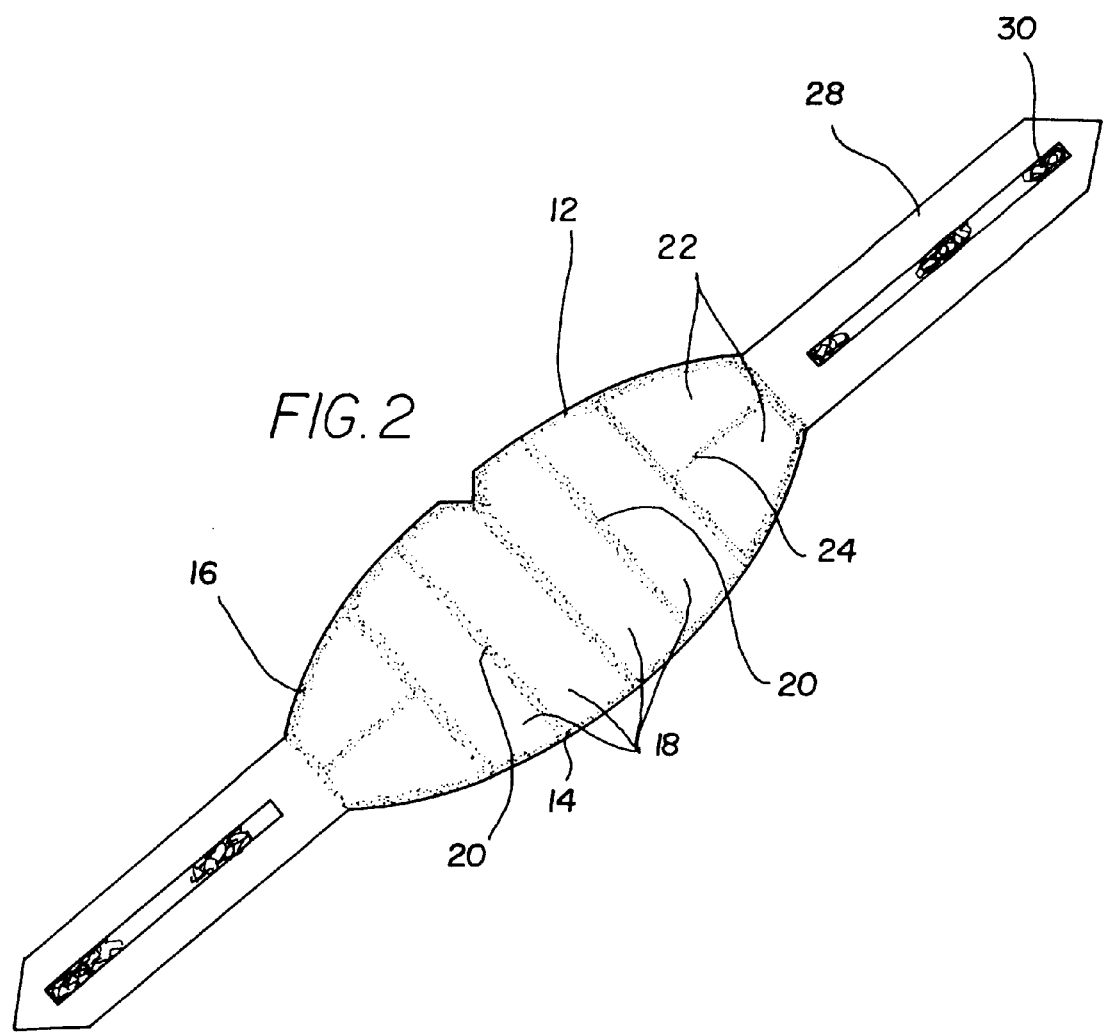
FIG. 2 is a top plan view of the present invention.

With reference now to the drawings, and in particular to FIGS. 1 through 4 thereof, a new therapeutic heat application device embodying the principles and concepts of the present invention and generally designated by the reference numeral 10 will be described.

As best illustrated in FIGS. 1 through 4, the therapeutic heat application device 10 comprises a pad portion 12 having a wide central portion 14 and a pair of opposed tapered side portions 16. The pad portion 12 has a shape resembling a pair of lips. The wide central portion 14 is divided into a plurality of narrow sections 18 by vertically extending seams 20. Each of the tapered side portions 16 is divided into two sections 22 by a horizontally extending seam 24. The sections 18,22 of the wide central portion 14 and the tapered side portions 16 are filled with a natural filler material 26 having a particulate or granular character. The seams 20,24 would maintain the proper positioning of the filler material 26 throughout the pad portion 12.

A pair of straps 28 extend outwardly from the tapered side portions 16 of the pad portion 12. Each of the straps 28 have hook and loop fasteners 30 disposed thereon for engaging each other when the straps 28 wrap the pad portion 12 around a body of a wearer. Alternate securement means besides hook and loop fasteners 30 could also be employed.

Most preferably, the natural filler material 26 comprises cracked corn 26, which is suitably stable and pliable when enclosed in the pad, heats uniformly when exposed to microwaves, and is also relatively low in cost. However, other less preferable natural materials that may be used in the pad include dried beans, peas, rice, and even sand.

In use, the present invention would be heated prior to use by placing the entire device 10 in a microwave oven. Note FIG. 4. The microwave oven should heat the device 10 in thirty second intervals taking approximately 2-½ to three minutes to heat. The heat would be retained by the pad portion 12 for approximately twenty minutes. Alternately, the pad portion 12 could be chilled for cold therapy. After removing the device 10 from the microwave, it could be applied to any area of the body requiring soothing heat. The pad portion 12 would be secured in place with the straps 28, ensuring the pad portion 12 remains comfortably in place.

As to a further discussion of the manner of usage and operation of the present invention, the same should be apparent from the above description. Accordingly, no further discussion relating to the manner of usage and operation will be provided.

With respect to the above description then, it is to be realized that the optimum dimensional relationships for the parts of the invention, to include variations in size, materials, shape, form, function and manner of operation, assembly and use, are deemed readily apparent and obvious to one skilled in the art, and all equivalent relationships to those illustrated in the drawings and described in the specification are intended to be encompassed by the present invention.

Therefore, the foregoing is considered as illustrative only of the principles of the invention. Further, since numerous modifications and changes will readily occur to those skilled in the art, it is not desired to limit the invention to the exact construction and operation shown and described, and accordingly, all suitable modifications and equivalents may be resorted to, falling within the scope of the invention.

I claim:

1. A therapeutic heat application device for applying heat to various areas of a person's body comprising, in combination:

a pad portion having a wide central portion and a pair of opposed tapered side portions, the pad portion having an interior and a generally elongate oval shape resembling a pair of lips, the wide central portion being divided into a plurality of narrow sections by laterally extending seams oriented perpendicular to a longitudinal extent of the wide central portion, the seams dividing the interior of the wide central portion into a plurality of separate narrow chambers having a heat retaining material therein such that the seams prevent movement of the heat retaining material from one of the chambers to an adjacent chamber, the narrow chambers partitioning in the lateral direction with respect to the generally elongate oval shape of the pad portion for facilitating curvature of the wide central portion such that the wide central portion is adapted for conforming to a curved area of a person's body, each of the tapered side portions being further divided into two sections by a horizontally extending seam; and a pair of straps extending outwardly in a longitudinal direction from the tapered side portions of the pad portion, each of the straps having hook and loop fasteners disposed thereon for engaging each other when the straps wrap the pad portion around a body of a wearer.

2. The therapeutic heat application device of claim 1, wherein said seams divide the interior of each of the side portions into a pair of separate chambers having a heat retaining material therein such that the seams prevent movement of the heat retaining material from one of the chambers to an adjacent chamber.

3. The therapeutic heat application device of claim 1, wherein the heat retaining material comprises cracked corn.

4. The therapeutic heat application device of claim 2, wherein the heat retaining material comprises cracked corn.

\* \* \* \* \*